United States Patent [19]

Zint

[11] 4,270,231

[45] Jun. 2, 1981

[54] PORTABLE MALE URINAL WITH DRAIN MEANS

[76] Inventor: Frederick J. Zint, 707 W. Riverside Dr., Jeffersonville, Ind. 47130

[21] Appl. No.: 78,666

[22] Filed: Sep. 24, 1979

[51] Int. Cl.[3] ........................ A47K 11/12; A61G 9/00; A61F 5/44

[52] U.S. Cl. ........................................ 4/144.1; 4/144.4; 4/455; 128/295

[58] Field of Search .............................. 4/144.1–144.4, 4/455, 450, 256, 507, 113.1, 114.1, 301, 640, 650; 128/295, 763, 766

[56] References Cited

U.S. PATENT DOCUMENTS

| | | | |
|---|---|---|---|
| 2,542,276 | 2/1951 | Felts | 4/144.3 |
| 2,582,398 | 1/1952 | Siegenthal | 4/144.3 X |
| 2,838,768 | 6/1958 | Fischett | 4/507 |
| 3,099,840 | 8/1963 | Johnson | 4/144.1 |
| 3,471,870 | 10/1969 | Segal | 4/144.1 X |
| 3,605,135 | 9/1971 | Tan | 4/256 |
| 3,727,244 | 4/1973 | Collins | 4/144.3 |
| 4,050,103 | 9/1977 | Nakao | 4/144.3 |
| 4,091,476 | 5/1978 | Deburgh | 4/144.3 |
| 4,117,845 | 10/1978 | Brown | 4/144.1 X |
| 4,121,306 | 10/1978 | Bringman et al. | 4/144.3 X |
| 4,187,562 | 2/1980 | Mioduski | 4/144.3 |

*Primary Examiner*—Stuart S. Levy
*Attorney, Agent, or Firm*—Richard L. Caslin

[57] ABSTRACT

A portable male urinal for use by bed-ridden patients is shown furnished with a drain hose to empty the contents of the urinal by gravity into a lower collection bag or receptacle. The end wall of the urinal has a recessed wall portion that supports a drain spout. A drain hose may be joined to the spout. The end wall has side notches for receiving the drain hose therethrough so the urinal may be supported upright on its end wall during non-use of the urinal. Other advantages are several species of closure means for the drain spout, elongated anchor means along the sides of the urinal for fastening the urinal to the user, and baffle means positioned within the urinal to discourage backflow of the contents.

10 Claims, 9 Drawing Figures

PORTABLE MALE URINAL WITH DRAIN MEANS

BACKGROUND OF THE INVENTION

1. Field of the Invention:

This invention relates to portable male urinals for use by bed-ridden patients or handicapped people, and particularly to such urinals that are furnished with a drain hose to empty the contents of the urinal by gravity into a lower collection bag or receptacle.

2. Description of the Prior Art:

It is widely known in the health care field to employ portable urinals for male bed-ridden patients. Frequently, part of the treatment of sick patients is that they drink large quantities of water and other liquids. Also certain X-ray procedures require the patient to abstain from solid foods and to limit all nourishment to liquids. Hence, the average bed-ridden patient generally handles more liquid than the average healthy person.

The Nakao et al. U.S. Pat. No. 4,050,103 describes a complex design of a combined portable male urinal having a drain hose that empties into a lower storage tank. This urinal has no means for supporting it upright on a bed-side table during non-use, nor is it a covered or closed urinal.

The De Burgh U.S. Pat. No. 4,091,476 also describes a portable male urinal that is provided with an overflow drain hose and an associated valve that is used to empty the urinal.

The Bringman et al. U.S. Pat. No. 4,121,306 also describes a portable male urinal having a drain hose with a three way valve and a reservoir as well as a sample container.

OBJECTS OF THE PRESENT INVENTION

The principle object of the present invention is to provide a portable male urinal with a connected drain hose which may be positioned upright on a supporting table during non-use.

A further object of the present invention is to provide a portable male urinal of the class described with a recessed drain spout having suitable closure means for use mainly when the drain hose is removed from the urinal.

A further object of the present invention is to provide a portable male urinal of the class described with a drain hose that may extend in various directions away from the urinal.

SUMMARY OF THE INVENTION

The present invention provides a portable male urinal having an end wall with a recessed wall portion supporting a drain spout for receiving a drain hose for emptying the contents of the urinal. The end wall is provided with side notch means for receiving the drain hose therethrough so the urinal may be positioned upright and supported on its end wall during non-use of the urinal.

BRIEF DESCRIPTION OF THE DRAWINGS

This invention will be better understood from the following description taken in conjunction with the accompanying drawings, and its scope will be pointed out in the appended claims.

DESCRIPTION OF THE PREFERRED EMBODIMENTS

Figure 1:
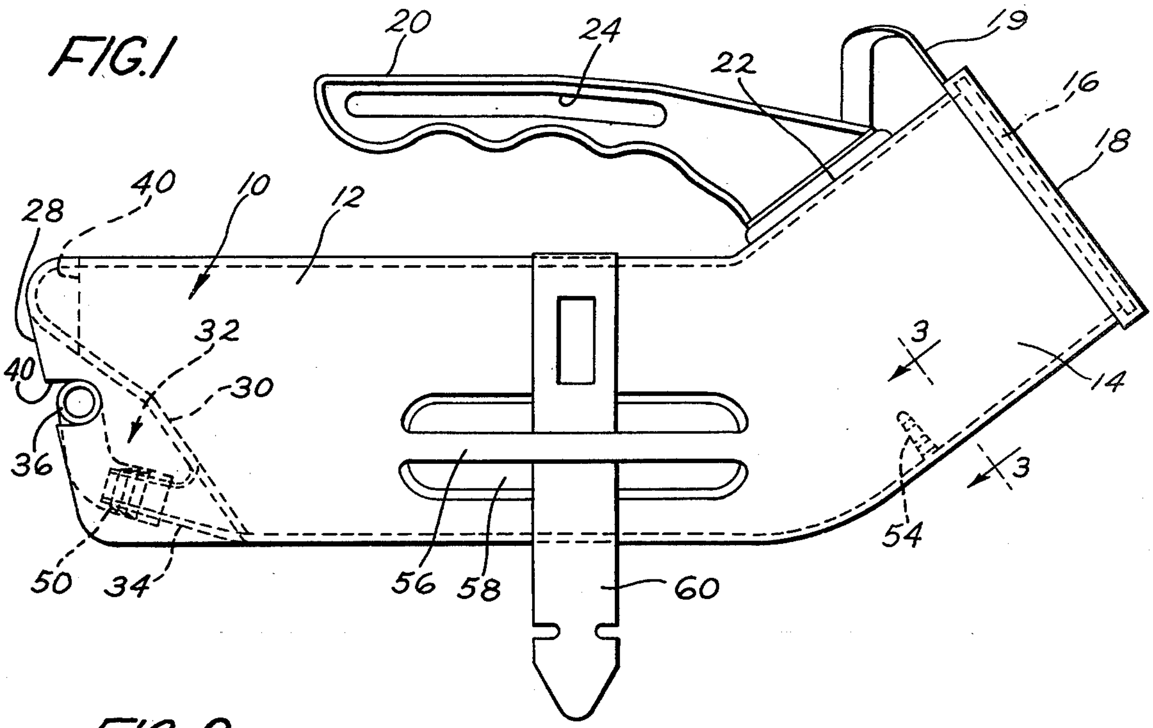
FIG. 1 is a side elevational view of a portable male urinal embodying the present invention showing a drain spout joined to a recessed end wall, and a drain hose fastened on the spout and extending out through a side notch so that the urinal may be supported upright on this end wall.
Figure 2:
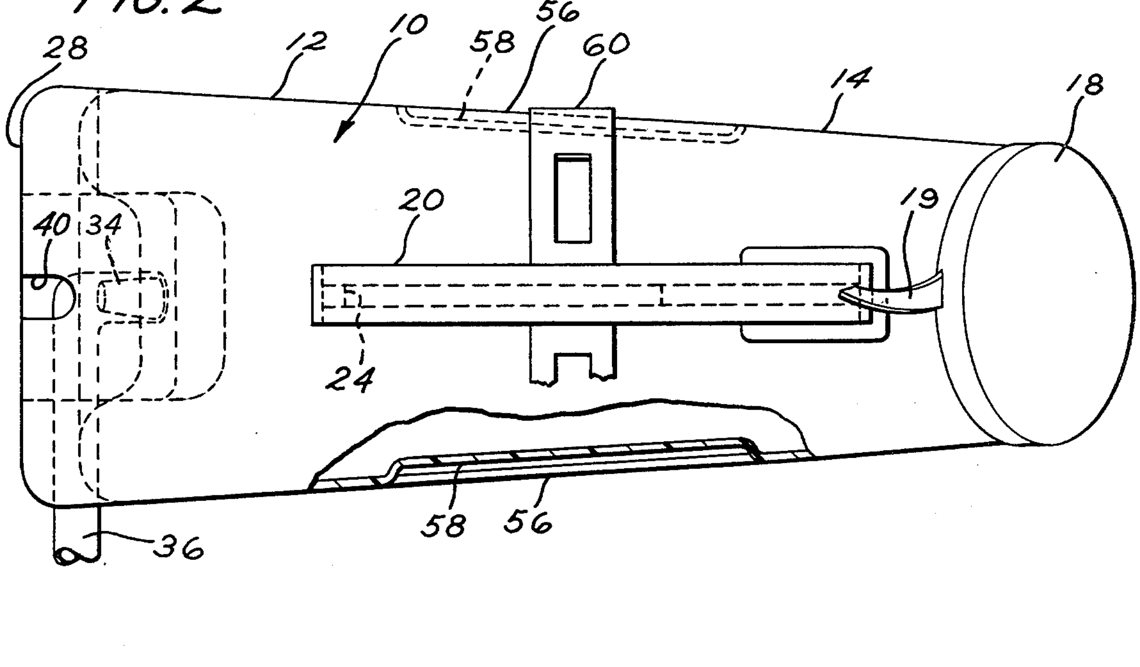
FIG. 2 is a top plan view of the urinal of FIG. 1.

Turning now to a consideration of the drawings and, in particular, to the side view of FIG. 1, there is shown a portable male urinal 10, that is shown in its use position. The urinal 10 is an elongate bottle-like container, of blow-molded polypropylene material, having a generally horizontal main body 12 and an upwardly inclined entrance end 14 that has an orifice 16 that is adapted to be closed by a removable snap-on cap or lid 18. A flexible attachment strap 19 joins the cap to the urinal to prevent losing the cap.

The top side of the urinal 10 is provided with a handle 20, that is formed of cantilever style, so that the handle may be hung over the side rails of the hospital bed out of sight, or the handle may be clipped onto the drawer handles of the bed-side table. Notice that the handle 20 is attached at 22 to the top side of the inclined entrance end 14 of the urinal. An elongated slot 24 is formed through the handle 20 for receiving a strap (not shown) so that the urinal may be attached to a leg of the user, if it were desirable.

Figure 4:
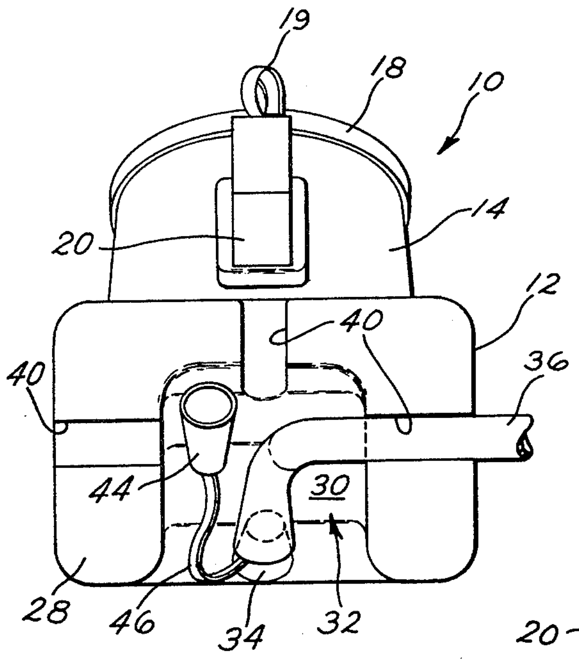
FIG. 4 is an end view of the urinal of FIG. 1, which also shows a removable cap for the drain spout for closing the spout when the drain hose is removed so as to continue to render the urinal operational without the drain hose.
Figure 6:
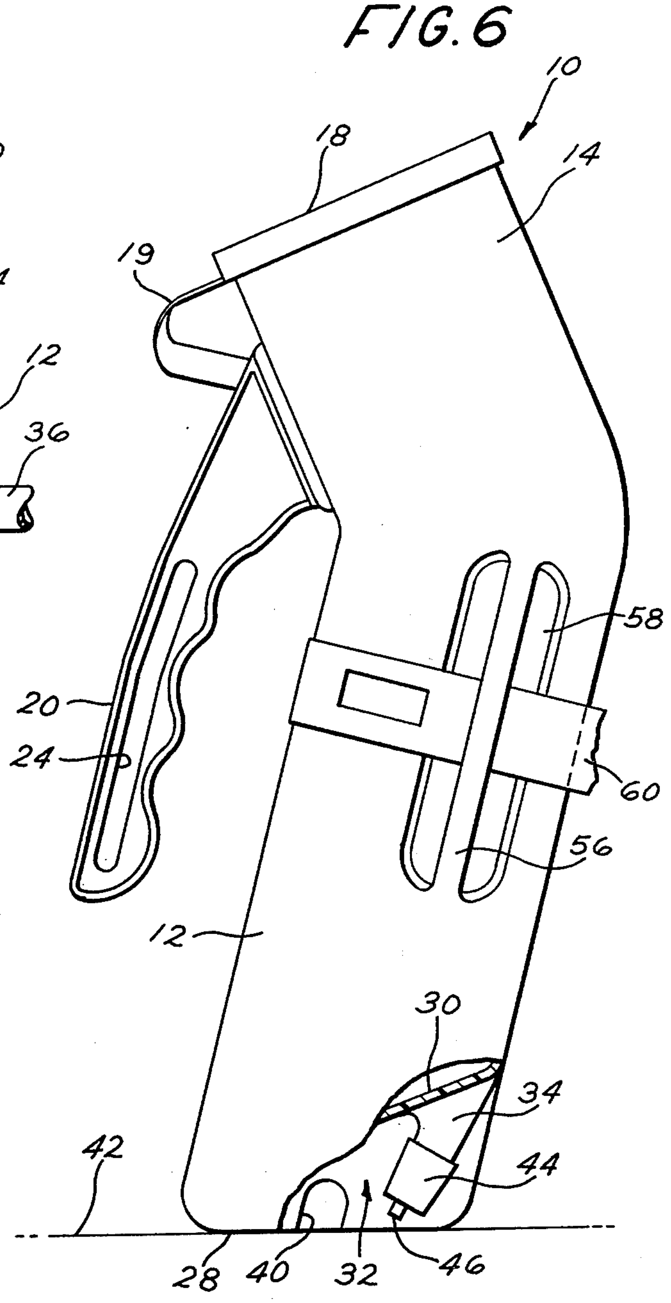
FIG. 6 is a view of the urinal of FIG. 1 shown supported in an upright non-use position, as for example on a bed-side table. The drain hose has been removed and the spout has been closed by the removable cap, that is best shown in the end view of FIG. 4.

An end wall 28 of the main body 12 is opposite the orifice 16. This end wall has a recessed wall portion 30 that forms a central concavity 32, as is best seen in FIG. 4. Joined to the lower end of the recessed wall portion is an inclined drain spout 34 for receiving a drain hose 36 thereover. The drain hose serves to empty the contents of the urinal by gravity into a lower receptacle. Side notches 40 are formed in the end wall 28 for receiving the drain hose 36 therethrough, as is best seen in FIG. 4. There is a side notch 40 leading to each side of the urinal, and one leading upwardly. These notches are for storing or capturing the drain hose when the urinal is to be set upright into its non-use position on a bed-side table 42, as is illustrated in FIG. 6. During normal use of the urinal, the drain hose 36 could and would just extend straight out from the drain spout 34 so as to drain off a maximum amount of the contents of the urinal, thereby leaving it substantially empty at all times.

It is well to provide the drain spout 34 with a closure means so that when the urinal is seldom used by the patient, the urinal 10 could be converted into a standard urinal that does not use a drain hose and additional receptacle or reservoir.

FIGS. 4 and 6 show one example of closure in the form of a snap-on cap 44 having a flexible attachment strap 46 joined to both the cap and the adjacent area of the urinal within the concavity 32.

Figure 8:
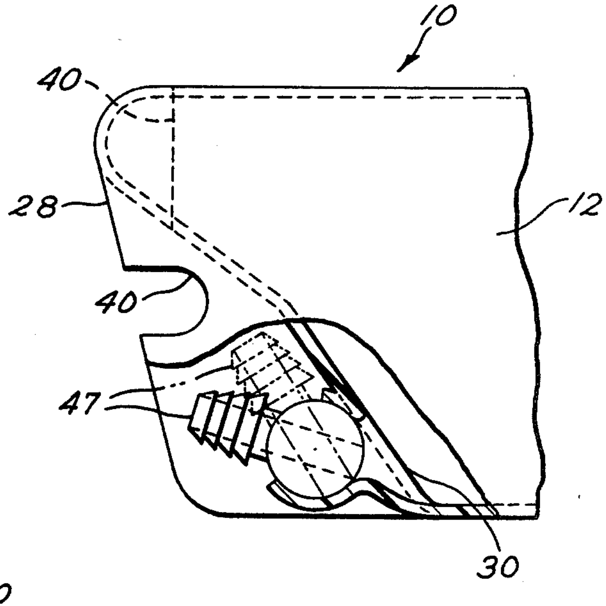
FIG. 8 is a fragmentary side view of the recessed end wall, similar to that of FIG. 7, except that the drain spout is hinged to the recessed wall so as to form a closure means for the spout in the nature of a hinged ON-OFF valve so the valve is open when it is extended, and the spout is closed when the spout is folded back into the recessed wall.

FIG. 8 shows a second sub-species of closure means in the form of a hinged drain spout 47 which is supported from the lower end of the recessed wall portion 30. This hinged spout 47 serves as a hinged ON-OFF valve so that the spout is open when it is extended outwardly, and the spout is closed when the spout is folded back into the recessed wall portion 30. Such a hinged valve is widely used for bottles of hand-care lotion.

Figure 9:
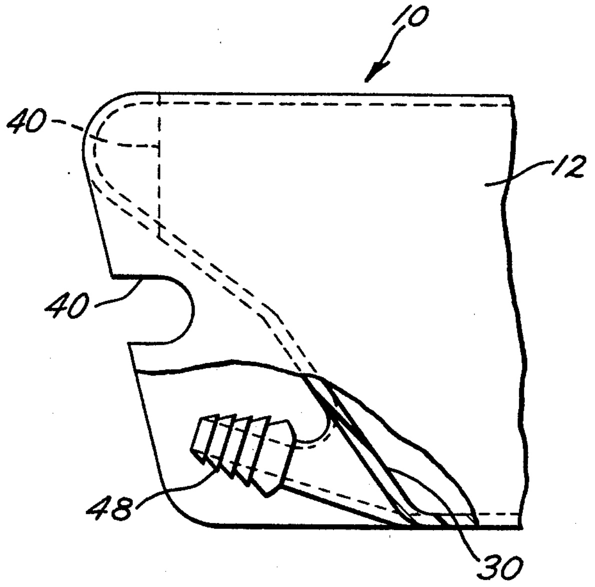
FIG. 9 is a fragmentary side view of the recessed end wall, similar to that of FIGS. 7 and 8, where the drain spout is furnished with a closure means of a push-pull ON-OFF valve.

FIG. 9 shows a third sub-species of closure means in the form of a two-piece drain spout 48 having a push-pull ON-OFF valve so that the spout is closed when the spout is pushed in, and the spout is opened when the spout is pulled out. Such a push-pull valve is widely used for dish washing detergent bottles.

Figure 7:
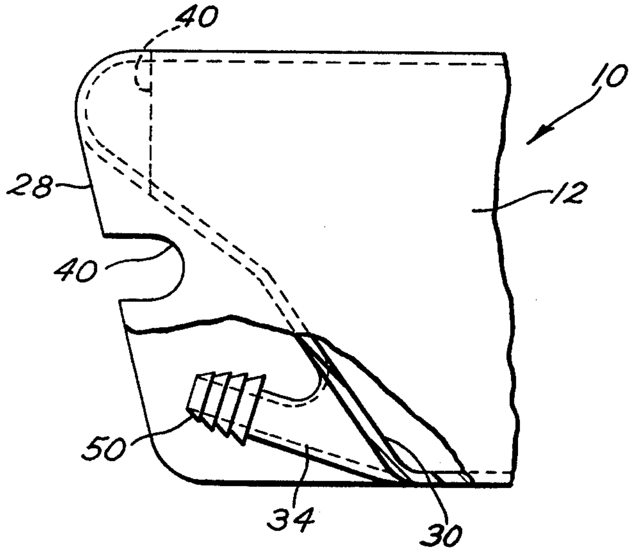
FIG. 7 is a fragmentary side view of the recessed end wall of the urinal of FIG. 1, with some parts broken away to show the inclined drain spout in full view.

As is best seen in FIG. 7, the drain spout 34 is provided with frusto-conical ribs 50 for receiving drain hoses of different size diameters. Such ribs are also shown in FIGS. 1, 8 and 9.

Figure 3:
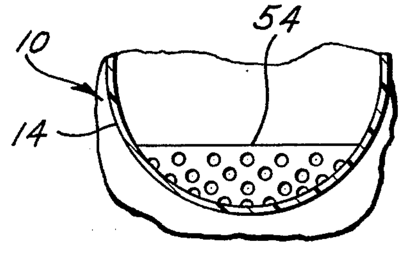
FIG. 3 is a fragmentary view taken on the line 3—3 of FIG. 1 to show the nature of a perforated baffle on the interior of the upwardly inclined entrance end of the urinal to prevent backflow of the contents of the urinal.

Looking at FIGS. 1 and 3, the interior of the urinal is provided with a perforated baffle 54 across the inclined bottom wall of the entrance end 14 so as to discourage backflow of the contents of the urinal.

The opposite sides of the urinal 10 are shown with elongated anchor means 56 which are each positioned over an elongated recess 58 in the side wall for receiving flexible strapping means 60 so that the urinal could be attached to a leg of the user in case of repeated usage or incontinence. While the anchor 56 and its cooperating recess 58 are shown near the mid-portion of the urinal, it will be understood by those skilled in the health care field that these elements 56 and 58 could be made to extend for nearly the complete length of the urinal for use in certain circumstances.

Figure 5:
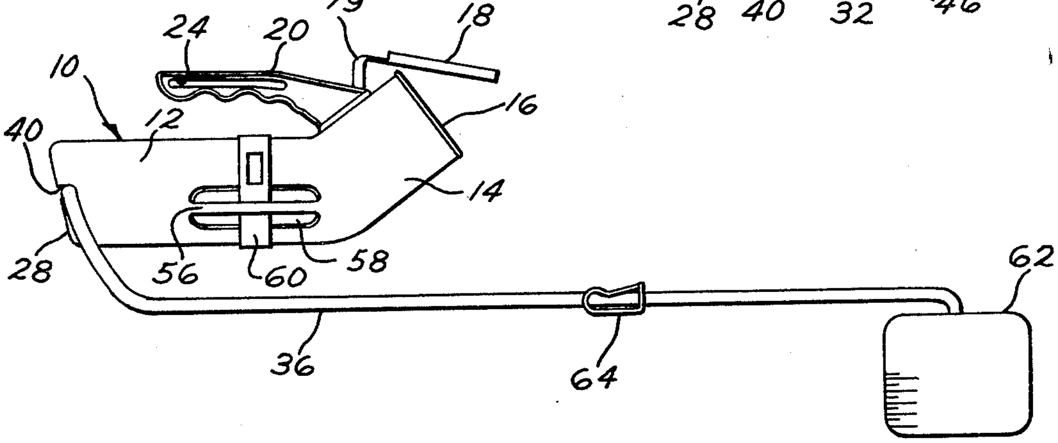
FIG. 5 is an assembly view on a reduced scale of the urinal system of the present invention comprising the portable urinal supplied with a drain hose that empties by gravity into a lower receptacle.

Turning to FIG. 5, the urinal 10 is shown with a drain hose 36 that empties into a lower bag or receptacle 62. A cut-off valve 64 is shown positioned on the drain hose for use in emptying the receptacle 62.

Modifications of this invention will occur to those skilled in this art. Therefore, it is to be understood that this invention is not limited to the particular embodiments disclosed, but that it is intended to cover all modifications which are within the true spirit and scope of this invention as claimed.

What is claimed is:

1. A portable male urinal comprising:

a. an elongate bottle-like container having a generally horizontal main body and an upwardly inclined entrance end that has an orifice that is adapted to be closed with a removable cap;

b. handle means supported from the urinal;

c. the end wall of the main body that is opposite the orifice having a recessed wall portion, a drain spout joined to the recessed wall portion near the bottom thereof so as not to protrude beyond the end wall; and d. a drain hose joined to the drain spout for emptying the contents of the urinal into a lower receptacle;

e. the said end wall portion of the main body being provided with side notch means adapted for receiving the drain hose therethrough when the urinal is positioned upright and supported on its end wall during non-use of the urinal.

2. The invention of claim 1, wherein the said drain spout is slightly upwardly inclined from the bottom wall of the urinal as well as being located within the recessed end wall configuration of the urinal.

3. The invention of claims 1 or 2, wherein the tip of the drain spout is provided with frusto-conical ribs for receiving drain tubing of different sizes.

4. The invention of claims 1 or 2 wherein the said side notch means are positioned in at least the opposite side portions of the urinal.

5. The invention of claim 1, wherein the drain spout is provided with integral closure means for sealing the spout when the drain hose is removed so that the urinal will continue to be operational, said integral closure means also being recessed within the end wall configuration of the urinal.

6. The invention of claim 5, wherein the said integral closure means is a removable cap that is attached by a flexible member adjacent to the drain spout.

7. The invention of claim 5, wherein the said integral closure means is a push-pull ON-OFF valve provided on the drain spout.

8. The invention of claim 5, wherein the said integral closure means is a hinged ON-OFF valve formed by hinging the drain spout to the said recessed wall portion so that the spout is open when it is extended, and the spout is closed when the spout is folded back into the recessed wall portion.

9. The invention of claim 1, wherein elongated anchor means is provided along at least one side of the urinal for receiving flexible strapping means so that the urinal may be fastened to the user.

10. The invention of claims 1 or 5 wherein a perforated interior baffle is positioned on the bottom surface of the upwardly inclined entrance end of the urinal to discourage backflow of the contents within the main body of the urinal.

* * * * *